United States Patent
Hecker

(10) Patent No.: US 7,147,371 B2
(45) Date of Patent: Dec. 12, 2006

(54) LASER GUIDES FOR X-RAY DEVICE

(76) Inventor: Joseph Hecker, 6030 Una-Del Dr., Rapid City, SD (US) 57702

(*) Notice: Subject to any disclaimer, the term of this patent is extended or adjusted under 35 U.S.C. 154(b) by 63 days.

(21) Appl. No.: 11/007,996

(22) Filed: Dec. 10, 2004

(65) Prior Publication Data

US 2006/0126796 A1 Jun. 15, 2006

(51) Int. Cl.
*A61B 6/08* (2006.01)

(52) U.S. Cl. ............... 378/206; 378/204; 378/205

(58) Field of Classification Search ............. 378/204, 378/205, 206; 33/286, 502, 503, DIG. 21
See application file for complete search history.

(56) References Cited

U.S. PATENT DOCUMENTS

| | | | | |
|---|---|---|---|---|
| 4,356,400 A | * | 10/1982 | Polizzi et al. | 378/138 |
| 4,426,726 A | * | 1/1984 | Cheetham | 378/206 |
| 4,836,671 A | * | 6/1989 | Bautista | 356/3.1 |
| 4,896,343 A | * | 1/1990 | Saunders | 378/95 |
| 5,320,111 A | * | 6/1994 | Livingston | 600/567 |
| 5,588,216 A | * | 12/1996 | Rank et al. | 33/286 |
| 5,606,590 A | * | 2/1997 | Petersen et al. | 378/177 |
| 5,707,360 A | * | 1/1998 | Rockseisen | 604/116 |
| 5,745,545 A | * | 4/1998 | Hughes | 378/65 |
| 6,041,249 A | * | 3/2000 | Regn | 600/429 |
| 6,044,291 A | * | 3/2000 | Rockseisen | 600/429 |
| 6,267,502 B1 | * | 7/2001 | McNeirney et al. | 378/206 |
| 6,447,164 B1 | * | 9/2002 | Polkus | 378/206 |
| 6,937,336 B1 | * | 8/2005 | Garcia et al. | 356/399 |
| 7,040,807 B1 | * | 5/2006 | Scheuering | 378/206 |
| 2003/0185349 A1 | * | 10/2003 | Roeckseisen | 378/206 |
| 2004/0141590 A1 | * | 7/2004 | Ihalainen | 378/206 |
| 2005/0155238 A1 | * | 7/2005 | Levine et al. | 33/286 |

* cited by examiner

*Primary Examiner*—Allen C. Ho
(74) *Attorney, Agent, or Firm*—Gene R. Woodle

(57) ABSTRACT

Laser guides for an X-ray device are disclosed in which a pair of laser projecting means are rotatably affixed to any X-ray device, either portable or stationary, such that the beams from the projecting means project toward the X-ray receptor and inward toward a line between the receptor and the X-ray device, and the laser beams cross at a particular location such that when the X-ray device is moved closer to or further from the X-ray receptor the laser beams cross when the X-ray device is at the optimum distance from the X-ray image receptor and the X-ray beam is centered upon the X-ray image receptor.

1 Claim, 1 Drawing Sheet

LASER GUIDES FOR X-RAY DEVICE

RELATED APPLICATIONS

This application relies for priority upon the Provisional Patent Application filed by Joseph Hecker entitled Laser Guides for X-ray Device, Ser. No. 60/528,097, filed Dec. 9, 2003.

BACKGROUND OF THE INVENTION

1. Field of the Invention

This invention relates generally to X-ray devices, and more particularly to a pair of laser guides which act to properly position an X-ray device.

2. Background Information

The use of X-rays in the treatment and diagnosis of patients is well known throughout the world. Generally, an X-ray apparatus includes an X-ray generator which generates an X-ray beam which is collimated by a collimator to the correct size field to pass through a patient's area of interest and produces an image on a receptor. In many cases, the receptor is film upon which an image of a patient's bones or other diagnostic areas are captured. The X-ray generation system, which may be either portable or stationary, usually includes a transformer and a generator to transform ordinarily available mains voltage to appropriate high voltage for generating X-rays. For obvious reasons it is imperative that the X-ray generator be aligned with the receptor.

In many cases a grid is interposed between the X-ray generator and the receptor to reduce the scatter associated with X-rays and produce a clearer image. Ordinarily, such a grid is formed of parallel strips of lead which are aligned vertically to a line between the X-ray generator and a given point on the grid. That is, while the rays projected directly beneath the X-ray generator are vertical, rays which intersect the grid intersect at an angle which becomes more acute the further they are away from vertical. Usually, if a grid is used, the X-ray system is aligned as follows: the X-ray generator, the portion of the patient to be X-rayed, the grid, and then the receptor (the receptor is most often referred to as "film"). The strips of the grid are parallel to each other and aligned with a line between the generator and any particular point on the film. Because lead blocks X-rays, the grid insures that only X-rays generally in a direct line between the X-ray generator and a particular area of the film reach the film. Random, non aligned, rays are blocked by the lead in the grid which reduces scatter and improves image quality.

Recently, digital X-ray receptors have been developed with which the X-ray image is produced in a digital form rather than upon X-ray film. X-ray apparatus may generally be categorized as either high energy or low energy units. High energy units are desirable, because they are capable of obtaining much clearer images, particularly when projected through thick areas of body mass. New high energy self contained X-ray systems which are relatively small, lightweight, portable, and include all elements in a single unit have been developed relatively recently.

One common application of X-rays involves the placement of the patient upon a table and projecting X-rays through the affected area of the patient's body and onto the receptor. It is imperative that the X-ray generator and receptor may be moved to position the device over the appropriate area without causing the patient to move unduly or be placed in an uncomfortable position. For purposes of this application, the term "patient" refers not only to human beings but to animals such as horses, dogs, etc. which may be X-rayed in the course of treatment by, for instance, veterinarians. For purposes of this application, all of the X-ray elements including the generator, transformer, and collimator, will be refereed to as the X-ray device.

In most instances, the patient is placed on some form of table with the X-ray device suspended above the table. The receptor and the grid are most often placed into a tray which is removably affixed to the table beneath the patient. In some cases the X-ray device is capable of being moved in two directions in relation to the length and width of the table which are considered the X and Y directions. The X-ray device is also, often, capable of being moved closer or further away from the patient (up and down) which is considered the Z direction. Although the above description assumes the table is horizontal, the "table" could be vertical or in some plane other than horizontal.

In most instances the X-ray device projects a set of "cross hairs" onto the table, image receptor, or the patient which help to align the X-ray device with the proper area of the patient. However, these cross hairs are often difficult to see in some lighting situations, particularly where the light is bright, and do not help with determining the proper distance between the X-ray device and the receptor. In order for the X-ray picture to be as clear and detailed as possible, it is important for the X-ray device to be the appropriate distance from the receptor.

Although the cross hair aiming method described above solves some problems relating to the correct positioning of the X-ray device in the X and Y direction, it does not work well in some lighting situations and does not solve problems relating to the correct positioning of the X-ray device in the Z direction.

The instant invention is a laser guide for an X-ray device which is unique, original, and solves all of the above noted problems relating properly positioning an X-ray device.

The ideal laser guides for an X-ray device should provide for the proper positioning of the X-ray device in the X and Y directions or along the length and width of an X-ray table. The ideal laser guides for an X-ray device should also be capable of being used to correctly position the X-ray device in the Z direction or closer or further from the patient and receptor. The ideal laser guides for an X-ray device should also be rugged, inexpensive, and easy to use.

SUMMARY OF THE INVENTION

The laser guides for an X-ray device provides a method of appropriately positioning an X-ray device, either portable or stationary, in three dimensions, referred to as the X, Y, and Z directions. The device includes a pair of mounting brackets which are affixed to either side of the X-ray device on opposite sides of the X-ray device. Most often this will be on the part of the X-ray device known as the collimator. In the preferred embodiment of the invention, the two brackets are aligned with the center line of the X-ray beam which projects from the X-ray device. The brackets may be placed on either the front and back of the X-ray device or on the sides.

A pair of lasers, which may be removable affixed to the brackets, are also provided. The lasers are conventional, self-contained, units which could be of the type used as laser sights for rifles or pistols. The lasers are affixed to the brackets such that they are generally rotatable in the direction of a vertical plane (plane one) passing through both brackets, but are not rotatable in a vertical plane (plane two) which is perpendicular to plane one. The beams of the lasers point generally downward, but may be adjusted such that they also point inward toward plane two near the surface of the X-ray table. The lasers may be calibrated and their angle adjusted such that when the lasers cross at an appropriate point when the X-ray device is the appropriate distance from the image receptor. That is, the beams of the lasers form the two equal legs of a downward pointing equilateral triangle with the base being a line between the lasers themselves.

In difficult lighting situations such as where the light is bright as in sunlight, the lasers beams are much easier to see than the conventional cross hairs projected by the X-ray device. In addition, when the angle of the lasers is properly calibrated, the position at which the laser beams cross may be used to insure that the X-ray device is the proper distance from the patient and the receptor and the X-ray beam is centered appropriately upon the image receptor.

One of the major objects of the present invention is to provide laser guides for an X-ray device which may be used to properly align the X-ray device with the position of the patient on an X-ray table.

Another object of the present invention is to provide laser guides which may be used to insure that the X-ray device is the appropriate distance from the patient and the receptor.

Another object of the present invention is to provide laser guides for an X-ray device which is rugged, inexpensive, and easy to use.

These and other features of the invention will become apparent when taken in consideration with the following detailed description and the drawings.

DESCRIPTION OF A PREFERRED EMBODIMENT

Figure 1:
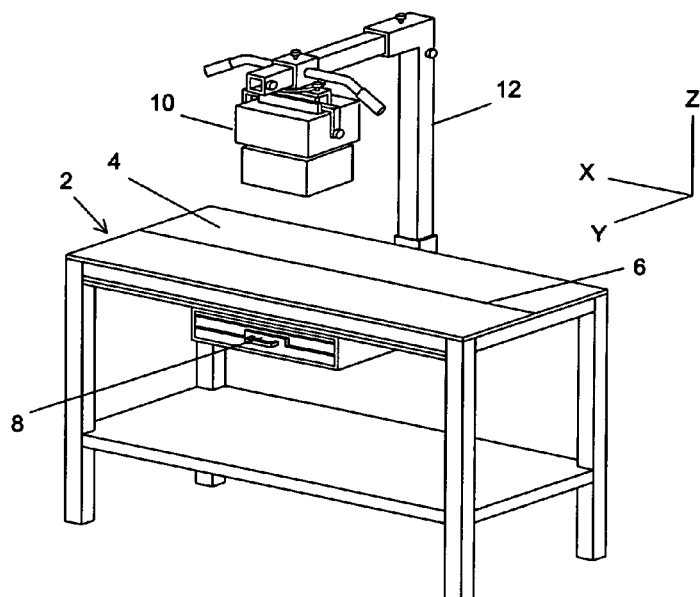
FIG. 1 is an isometric view of a typical X-ray device set up with an X-ray table.

Referring to the drawing FIG. 1, there is shown an isometric view of a typical X-ray device and X-ray table. The table 2 may have many forms, but ordinarily includes a top 4. In many cases, there is an alignment line 6 down the centerline of the top 4. Typically, the grid (not shown) and the receptor (not shown) are affixed to the underside of said top 4 in a tray 8. The X-ray device 10 is often mounted on an arm 12 such that the X-ray device 10 is movable up and down in the Z direction and back and forth in the X and Y directions. For obvious reasons, said X-ray device 10 must be properly positioned in the X and Y directions to take an X-ray of the appropriate portion of the patient. In order for the X-ray to be as clear and detailed as possible, said X-ray device 10 must also be positioned at the correct height in the Z direction. Although the drawings and description describe said top 4 as being horizontal, the instant invention would work equally well for a top and aligned X-ray device at any angle.

Figure 2:
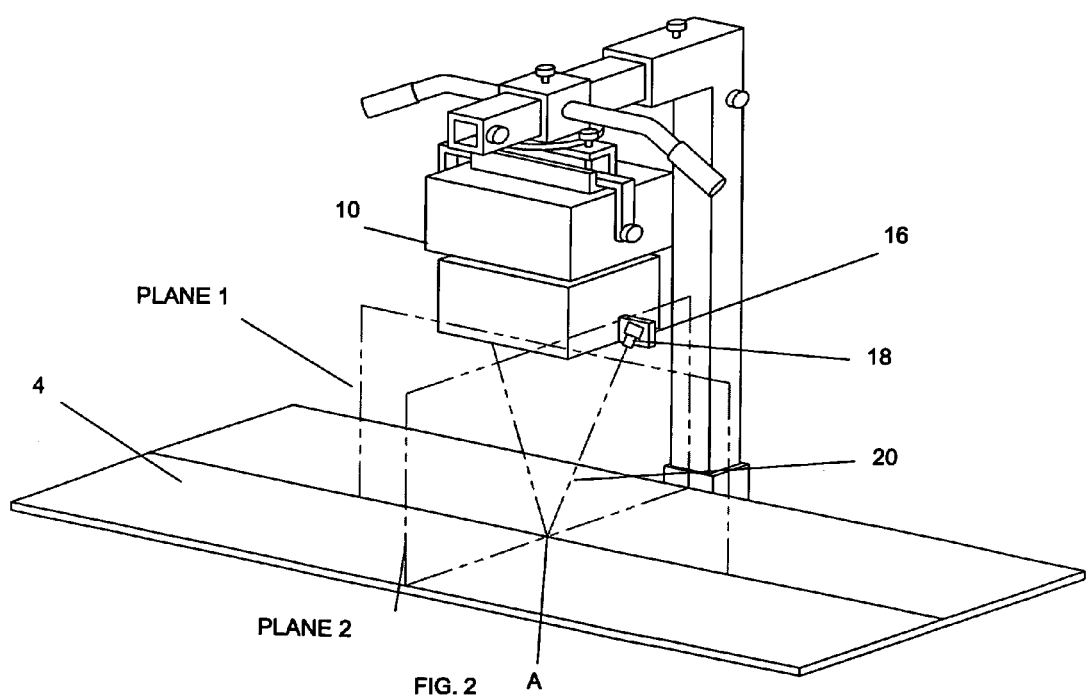
FIG. 2 is an isometric view of a typical X-ray device with the laser guides installed.

Referring now to FIG. 2, said X-ray device 10 is shown with the laser guides for X-ray device installed. A pair of brackets 16 are affixed to said X-ray device 10 on opposite sides of and centered upon said X-ray device 10. The brackets 16 are shown are being parallel to the X-Z plane (plane 1), but could also be affixed parallel to the Y-Z plane (plane 2). In the preferred embodiment of the invention, said brackets 16 are affixed near the bottom of said X-ray device 10, on the collimator. A pair of lasers 18 are movably affixed to said brackets 16. The lasers 18 are rotatable in plane 1, but are immobile in the direction of plane 2. The laser beams 20 project generally downward; but, when said lasers 18 are rotated, also project inward towards plane two near where plane two intersects said top 4.

Still referring to FIG. 2, said lasers 18 may be calibrated and rotated such that said laser beams 20 cross or intersect at a point such as point A on the top surface of said top 4. When said lasers 18 are appropriately calibrated and rotated, and point A is at the appropriate location (on the top surface of said top 4, for instance) said X-ray device 10 is automatically positioned at the appropriate height above said top 4. That is, said X-ray device 10 is in the appropriate position relative to the Z axis. Said X-ray device 10 may also be moved in the X or Y directions, using point A as a guide, to appropriately position said X-ray device 10 relative to both the X and Y axis.

In operation, the rotation of said lasers 18 is calibrated such that, when said laser beams 20 cross at a known point, said X-ray device 10 is at the appropriate height above said top 4. Using the crossing point of said laser beams 20 as a guide, said X-ray device 10 may also be appropriately positioned in the X-Y plane upon the surface of said top 4. It should be understood that positioning said X-ray device 10 as described above actually positions said X-ray device appropriately with the X-ray image receptor.

In the prefered embodiment of the instant invention, all parts and elements are conventional and may be obtained from many sources.

While preferred embodiments of this invention have been shown and described above, it will be apparent to those skilled in the art that various modifications may be made in these embodiments without departing from the spirit of the present invention.

I claim:

1. A laser guided X-ray device, comprising:
    (1) an X-ray device, the X-ray device being aimed at and aligned with a receptor, and the x-ray device having an emitter capable of projecting an X-ray beam through a patient or object and creating an X-ray image of such patient or object upon said receptor, and the x-ray device further being capable of being moved closer to or further from said receptor such that said X-ray device is at the optimum distance from said receptor and the X-ray beam is centered upon the receptor to create a clear and focused X-ray image;
    (2) a pair of brackets affixed to said X-ray device, or an any attachment which moves in concert with said X-ray device, such that the X-ray device emitter and the two brackets are in the same plane, which plane is perpendicular to said receptor, and one of said brackets being on either side of said emitter; and
    (3) a pair of laser beam projecting means, one being rotatably affixed to each of said brackets such that the laser beam projecting means are capable of being rotated parallel to said plane and affixed in a position after being rotated, and each of said laser beam projecting means projects a laser beam toward said receptor and inward toward a line between said emitter and the center of said receptor such that the laser beams cross at a visible location and said laser beam projecting means may be rotated and affixed at a position such that said laser beams cross at an appropriate location which insured that said X-ray device is at the appropriate distance from said receptor and the x-ray beam is centered upon said receptor to insure that a clear and focused X-ray image is produced when the X-ray device is used;

whereby, after said laser beam projecting means are properly calibrated, said X-ray device may be moved closer to or further away from said receptor until said laser beams cross at an appropriate location and the operator may be assured that said X-ray device is at the proper location from said receptor to take a clear and focused X-ray image.

* * * * *